(12) United States Patent
Mathis et al.

(10) Patent No.: US 10,052,205 B2
(45) Date of Patent: Aug. 21, 2018

(54) FIXED ANCHOR AND PULL MITRAL VALVE DEVICE AND METHOD

(71) Applicant: CARDIAC DIMENSIONS PTY. LTD., Kirkland, WA (US)

(72) Inventors: Mark L. Mathis, Fremont, CA (US); Gregory D. Nieminen, Bothell, WA (US); David G. Reuter, Bothell, WA (US)

(73) Assignee: Cardiac Dimensions Pty. Ltd., Kirkland, WA (US)

( * ) Notice: Subject to any disclaimer, the term of this patent is extended or adjusted under 35 U.S.C. 154(b) by 0 days.

(21) Appl. No.: 15/230,093

(22) Filed: Aug. 5, 2016

(65) Prior Publication Data

US 2016/0338833 A1    Nov. 24, 2016

Related U.S. Application Data

(60) Continuation of application No. 12/016,054, filed on Jan. 17, 2008, now Pat. No. 9,408,695, which is a
(Continued)

(51) Int. Cl.
*A61F 2/24* (2006.01)
*A61B 17/00* (2006.01)
*A61N 1/05* (2006.01)

(52) U.S. Cl.
CPC .......... *A61F 2/2451* (2013.01); *A61F 2/2442* (2013.01); *A61F 2/2466* (2013.01);
(Continued)

(58) Field of Classification Search
CPC .... A61F 2/2442; A61F 2/2451; A61F 2/2466; A61F 2/2427
See application file for complete search history.

(56) References Cited

U.S. PATENT DOCUMENTS

| | | |
|---|---|---|
| 3,620,212 A | 11/1971 | Fannon, Jr. et al. |
| 3,786,806 A | 1/1974 | Johnson et al. |

(Continued)

FOREIGN PATENT DOCUMENTS

| | | |
|---|---|---|
| EP | 0893133 A1 | 1/1999 |
| EP | 0903110 A1 | 3/1999 |
| EP | 0968688 A1 | 1/2000 |
| EP | 1050274 A1 | 11/2000 |
| EP | 1095634 A2 | 5/2001 |
| EP | 1177779 A2 | 2/2002 |
| EP | 2181670 A2 | 5/2010 |
| GB | 0741604 | 12/1955 |
| JP | 2754067 | 3/1998 |
| JP | 2000-308652 | 11/2000 |
| JP | 2001-503291 | 3/2001 |
| JP | 2003-503101 | 1/2003 |
| JP | 2003-521310 | 7/2003 |

(Continued)

OTHER PUBLICATIONS

El-Maasarany et al.; The coronary sinus conduit function: Anatomical study (relationship to adjacent structures); http://europace.oxfordjournals.org/cge/content/full/7/5/475. (accessed Sep. 9, 2008).

(Continued)

*Primary Examiner* — Howie Matthews
(74) *Attorney, Agent, or Firm* — Shay Glenn LLP

(57) ABSTRACT

Devices for treating mitral valve regurgitation, including a distal expandable anchor, a proximal expandable anchor, and a fixed length connecting member extending from the proximal expandable anchor to the distal expandable anchor, where at least one of the proximal and distal anchors includes first and second arm segments that extend from one end of the device toward the connecting member and the other anchor when in a collapsed delivery configuration, and where the at least one of the proximal and distal anchors that comprises the first and second arm segments has an expanded configuration in which the first and second arm segments extend radially outwardly such that the first and second arm segments extend away from one another toward the connector, and meet one another at a location axially spaced from the end of the device.

6 Claims, 4 Drawing Sheets

Related U.S. Application Data division of application No. 11/132,788, filed on May 18, 2005, now abandoned, which is a continuation of application No. 10/066,426, filed on Jan. 30, 2002, now Pat. No. 6,976,995.

(52) U.S. Cl.
CPC ....... *A61B 2017/00243* (2013.01); *A61F 2/24* (2013.01); *A61F 2210/0014* (2013.01); *A61F 2220/0008* (2013.01); *A61F 2250/0012* (2013.01); *A61F 2310/00017* (2013.01); *A61F 2310/00023* (2013.01); *A61N 1/057* (2013.01); *A61N 2001/0585* (2013.01)

(56) References Cited

U.S. PATENT DOCUMENTS

| | | |
|---|---|---|
| 3,890,977 A | 6/1975 | Wilson |
| 3,974,526 A | 8/1976 | Dardik et al. |
| 3,995,623 A | 12/1976 | Blake et al. |
| 4,055,861 A | 11/1977 | Carpentier et al. |
| 4,164,046 A | 8/1979 | Cooley |
| 4,485,816 A | 12/1984 | Krumme |
| 4,550,870 A | 11/1985 | Krumme et al. |
| 4,588,395 A | 5/1986 | Lemelson |
| 4,830,023 A | 5/1989 | de Toledo et al. |
| 5,061,277 A | 10/1991 | Carpentier et al. |
| 5,099,838 A | 3/1992 | Bardy |
| 5,104,404 A | 4/1992 | Wolff |
| 5,197,978 A | 3/1993 | Hess |
| 5,250,071 A | 10/1993 | Palermo |
| 5,261,916 A | 11/1993 | Engelson |
| 5,265,601 A | 11/1993 | Mehra |
| 5,344,426 A | 9/1994 | Lau et al. |
| 5,350,420 A | 9/1994 | Cosgrove et al. |
| 5,411,549 A | 5/1995 | Peters |
| 5,433,727 A | 7/1995 | Sideris |
| 5,441,515 A | 8/1995 | Khosravi et al. |
| 5,449,373 A | 9/1995 | Pinchasik et al. |
| 5,454,365 A | 10/1995 | Bonutti |
| 5,458,615 A | 10/1995 | Klemm et al. |
| 5,474,557 A | 12/1995 | Mai |
| 5,507,295 A | 4/1996 | Skidmore |
| 5,507,802 A | 4/1996 | Imran |
| 5,514,161 A | 5/1996 | Limousin |
| 5,554,177 A | 9/1996 | Kieval et al. |
| 5,562,698 A | 10/1996 | Parker |
| 5,575,818 A | 11/1996 | Pinchuk |
| 5,584,867 A | 12/1996 | Limousin et al. |
| 5,601,600 A | 2/1997 | Ton |
| 5,617,854 A | 4/1997 | Munsif |
| 5,662,703 A | 9/1997 | Yurek et al. |
| 5,676,671 A | 10/1997 | Inoue |
| 5,733,325 A | 3/1998 | Robinson et al. |
| 5,733,328 A | 3/1998 | Fordenbacher |
| 5,741,297 A | 4/1998 | Simon |
| 5,752,969 A | 5/1998 | Cunci et al. |
| 5,800,519 A | 9/1998 | Sandock |
| 5,824,071 A | 10/1998 | Nelson et al. |
| 5,836,882 A | 11/1998 | Frazin |
| 5,871,501 A | 2/1999 | Leschinsky et al. |
| 5,891,193 A | 4/1999 | Robinson et al. |
| 5,895,391 A | 4/1999 | Farnholtz |
| 5,899,882 A | 5/1999 | Waksman et al. |
| 5,908,404 A | 6/1999 | Elliot |
| 5,928,258 A | 7/1999 | Khan et al. |
| 5,935,161 A | 8/1999 | Robinson et al. |
| 5,954,761 A | 9/1999 | Machek et al. |
| 5,961,545 A | 10/1999 | Lentz et al. |
| 5,978,705 A | 11/1999 | KenKnight et al. |
| 5,984,944 A | 11/1999 | Forber |
| 6,001,118 A | 12/1999 | Daniel et al. |
| 6,007,519 A | 12/1999 | Rosselli |
| 6,015,402 A | 1/2000 | Sahota |
| 6,022,371 A | 2/2000 | Killion |
| 6,027,517 A | 2/2000 | Crocker et al. |
| 6,045,497 A | 4/2000 | Schweich, Jr. et al. |
| 6,053,900 A | 4/2000 | Brown et al. |
| 6,056,775 A | 5/2000 | Borghi et al. |
| 6,077,295 A | 6/2000 | Limon et al. |
| 6,077,297 A | 6/2000 | Robinson et al. |
| 6,080,182 A | 6/2000 | Shaw et al. |
| 6,086,611 A | 7/2000 | Duffy et al. |
| 6,096,064 A | 8/2000 | Routh |
| 6,099,549 A | 8/2000 | Bosma et al. |
| 6,099,552 A | 8/2000 | Adams |
| 6,129,755 A | 10/2000 | Mathis et al. |
| 6,159,220 A | 12/2000 | Gobron et al. |
| 6,162,168 A | 12/2000 | Schweich, Jr. et al. |
| 6,171,320 B1 | 1/2001 | Monassevitch |
| 6,183,512 B1 | 2/2001 | Howanec et al. |
| 6,190,406 B1 | 2/2001 | Duerig et al. |
| 6,200,336 B1 | 3/2001 | Pavcnik et al. |
| 6,210,432 B1 | 4/2001 | Solem et al. |
| 6,228,098 B1 | 5/2001 | Kayan et al. |
| 6,241,757 B1 | 6/2001 | An et al. |
| 6,254,628 B1 | 7/2001 | Wallace et al. |
| 6,267,783 B1 | 7/2001 | Letendre et al. |
| 6,275,730 B1 | 8/2001 | KenKnight et al. |
| 6,306,141 B1 | 10/2001 | Jervis |
| 6,312,446 B1 | 11/2001 | Huebsch et al. |
| 6,334,864 B1 | 1/2002 | Amplatz et al. |
| 6,342,067 B1 | 1/2002 | Mathis et al. |
| 6,345,198 B1 | 2/2002 | Mouchawar et al. |
| 6,352,553 B1 | 3/2002 | van der Burg et al. |
| 6,352,561 B1 | 3/2002 | Leopold et al. |
| 6,358,195 B1 | 3/2002 | Green et al. |
| 6,368,345 B1 | 4/2002 | Dehdashtian et al. |
| 6,395,017 B1 | 5/2002 | Dwyer et al. |
| 6,402,781 B1 | 6/2002 | Langberg et al. |
| 6,409,750 B1 | 6/2002 | Hyodoh et al. |
| 6,419,696 B1 | 7/2002 | Ortiz et al. |
| 6,442,427 B1 | 8/2002 | Boute et al. |
| 6,464,720 B2 | 10/2002 | Boatman et al. |
| 6,478,776 B1 | 11/2002 | Rosenman et al. |
| 6,503,271 B2 | 1/2003 | Duerig et al. |
| 6,537,314 B2 | 3/2003 | Langberg et al. |
| 6,556,873 B1 | 4/2003 | Smits |
| 6,562,066 B1 | 5/2003 | Martin |
| 6,562,067 B2 | 5/2003 | Mathis |
| 6,569,198 B1 | 5/2003 | Wilson et al. |
| 6,589,208 B2 | 7/2003 | Ewers et al. |
| 6,599,314 B2 | 7/2003 | Mathis et al. |
| 6,602,288 B1 | 8/2003 | Cosgrove et al. |
| 6,602,289 B1 | 8/2003 | Colvin et al. |
| 6,623,521 B2 | 9/2003 | Steinke et al. |
| 6,626,899 B2 | 9/2003 | Houser et al. |
| 6,629,534 B1 | 10/2003 | St. Goar et al. |
| 6,629,994 B2 | 10/2003 | Gomez et al. |
| 6,643,546 B2 | 11/2003 | Mathis et al. |
| 6,648,881 B2 | 11/2003 | KenKnight et al. |
| 6,652,538 B2 | 11/2003 | Kayan et al. |
| 6,656,221 B2 | 12/2003 | Taylor et al. |
| 6,676,702 B2 | 1/2004 | Mathis |
| 6,689,164 B1 | 2/2004 | Seguin |
| 6,709,425 B2 | 3/2004 | Gambale et al. |
| 6,716,158 B2 | 4/2004 | Raman et al. |
| 6,718,985 B2 | 4/2004 | Hlavka et al. |
| 6,721,598 B1 | 4/2004 | Helland et al. |
| 6,723,038 B1 | 4/2004 | Schroeder et al. |
| 6,733,521 B2 | 5/2004 | Chobotov et al. |
| 6,743,219 B1 | 6/2004 | Dwyer et al. |
| 6,764,510 B2 | 7/2004 | Vidlund et al. |
| 6,773,446 B1 | 8/2004 | Dwyer et al. |
| 6,776,784 B2 | 8/2004 | Ginn |
| 6,790,231 B2 | 9/2004 | Liddicoat et al. |
| 6,793,673 B2 | 9/2004 | Kowalsky et al. |
| 6,797,001 B2 | 9/2004 | Mathis et al. |
| 6,798,231 B2 | 9/2004 | Iwasaki et al. |
| 6,800,090 B2 | 10/2004 | Alferness et al. |
| 6,805,128 B1 | 10/2004 | Pless et al. |
| 6,810,882 B2 | 11/2004 | Langberg et al. |
| 6,821,297 B2 | 11/2004 | Snyders |

(56) References Cited

U.S. PATENT DOCUMENTS

| | | | |
|---|---|---|---|
| 6,824,562 B2 | 11/2004 | Mathis et al. |
| 6,881,220 B2 | 4/2005 | Edwin et al. |
| 6,890,353 B2 | 5/2005 | Cohn et al. |
| 6,899,734 B2 | 5/2005 | Castro et al. |
| 6,908,478 B2 | 6/2005 | Alferness et al. |
| 6,926,690 B2 | 8/2005 | Renati |
| 6,935,404 B2 | 8/2005 | Duerig et al. |
| 6,949,122 B2 | 9/2005 | Adams et al. |
| 6,955,689 B2 | 10/2005 | Ryan et al. |
| 6,960,229 B2 | 11/2005 | Mathis et al. |
| 6,964,683 B2 | 11/2005 | Kowalsky et al. |
| 6,966,926 B2 | 11/2005 | Mathis |
| 6,976,995 B2 | 12/2005 | Mathis et al. |
| 7,004,958 B2 | 2/2006 | Adams et al. |
| 7,152,605 B2 | 12/2006 | Khairkhahan et al. |
| 7,175,653 B2 | 2/2007 | Gaber |
| 7,179,282 B2 | 2/2007 | Alferness et al. |
| 7,270,676 B2 | 9/2007 | Alferness et al. |
| 7,309,354 B2 | 12/2007 | Mathis et al. |
| 7,311,729 B2 | 12/2007 | Mathis et al. |
| 7,316,708 B2 | 1/2008 | Gordon et al. |
| 7,364,588 B2 | 4/2008 | Mathis et al. |
| 7,452,375 B2 | 11/2008 | Mathis et al. |
| 7,503,931 B2 | 3/2009 | Kowalsky et al. |
| 7,591,826 B2 | 9/2009 | Alferness et al. |
| 7,608,102 B2 | 10/2009 | Adams et al. |
| 7,635,387 B2 | 12/2009 | Reuter et al. |
| 7,674,287 B2 | 3/2010 | Alferness et al. |
| 7,758,639 B2 | 7/2010 | Mathis |
| 7,814,635 B2 | 10/2010 | Gordon |
| 7,828,841 B2 | 11/2010 | Mathis et al. |
| 7,828,842 B2 | 11/2010 | Nieminen et al. |
| 7,828,843 B2 | 11/2010 | Alferness et al. |
| 7,837,728 B2 | 11/2010 | Nieminen et al. |
| 7,837,729 B2 | 11/2010 | Gordon et al. |
| 7,887,582 B2 | 2/2011 | Mathis et al. |
| 8,006,594 B2 | 8/2011 | Hayner et al. |
| 8,062,358 B2 | 11/2011 | Mathis et al. |
| 8,075,608 B2 | 12/2011 | Gordon et al. |
| 8,172,898 B2 | 5/2012 | Alferness et al. |
| 8,182,529 B2 | 5/2012 | Gordon et al. |
| 8,439,971 B2 | 5/2013 | Reuter et al. |
| 8,974,525 B2 | 3/2015 | Nieminen et al. |
| 9,320,600 B2 | 4/2016 | Nieminen et al. |
| 9,408,695 B2 | 8/2016 | Mathis et al. |
| 2001/0018611 A1 | 8/2001 | Solem et al. |
| 2001/0041899 A1 | 11/2001 | Foster |
| 2001/0044568 A1 | 11/2001 | Langberg et al. |
| 2001/0049558 A1 | 12/2001 | Liddicoat et al. |
| 2002/0016628 A1 | 2/2002 | Langberg et al. |
| 2002/0042621 A1 | 4/2002 | Liddicoat et al. |
| 2002/0042651 A1 | 4/2002 | Liddicoat et al. |
| 2002/0049468 A1 | 4/2002 | Streeter et al. |
| 2002/0055774 A1 | 5/2002 | Liddicoat |
| 2002/0065554 A1 | 5/2002 | Streeter |
| 2002/0095167 A1 | 7/2002 | Liddicoat et al. |
| 2002/0138044 A1 | 9/2002 | Streeter et al. |
| 2002/0151961 A1 | 10/2002 | Lashinski et al. |
| 2002/0156526 A1 | 10/2002 | Hlavka et al. |
| 2002/0161377 A1 | 10/2002 | Rabkin et al. |
| 2002/0161393 A1 | 10/2002 | Demond et al. |
| 2002/0183837 A1 | 12/2002 | Streeter et al. |
| 2002/0183838 A1 | 12/2002 | Liddicoat et al. |
| 2002/0183841 A1 | 12/2002 | Cohn et al. |
| 2002/0188170 A1 | 12/2002 | Santamore et al. |
| 2002/0193827 A1 | 12/2002 | McGuckin et al. |
| 2003/0018358 A1 | 1/2003 | Saadat |
| 2003/0040771 A1 | 2/2003 | Hyodoh et al. |
| 2003/0069636 A1 | 4/2003 | Solem et al. |
| 2003/0078465 A1 | 4/2003 | Pai et al. |
| 2003/0078654 A1 | 4/2003 | Taylor et al. |
| 2003/0083613 A1 | 5/2003 | Schaer |
| 2003/0088305 A1 | 5/2003 | Van Schie et al. |
| 2003/0093148 A1 | 5/2003 | Bolling et al. |
| 2003/0130730 A1 | 7/2003 | Cohn et al. |
| 2004/0019377 A1 | 1/2004 | Taylor et al. |
| 2004/0039443 A1 | 2/2004 | Solem et al. |
| 2004/0102840 A1 | 5/2004 | Solem et al. |
| 2004/0133220 A1 | 7/2004 | Lashinski et al. |
| 2004/0133240 A1 | 7/2004 | Adams et al. |
| 2004/0153147 A1 | 8/2004 | Mathis |
| 2004/0158321 A1 | 8/2004 | Reuter et al. |
| 2004/0176840 A1 | 9/2004 | Langberg |
| 2004/0193260 A1 | 9/2004 | Alferness et al. |
| 2004/0220654 A1 | 11/2004 | Mathis et al. |
| 2004/0220657 A1 | 11/2004 | Nieminen et al. |
| 2004/0260342 A1 | 12/2004 | Vargas et al. |
| 2005/0004667 A1 | 1/2005 | Swinford et al. |
| 2005/0027351 A1 | 2/2005 | Reuter et al. |
| 2005/0033419 A1 | 2/2005 | Alferness et al. |
| 2005/0060030 A1 | 3/2005 | Lashinski et al. |
| 2005/0096740 A1 | 5/2005 | Langberg et al. |
| 2005/0137449 A1 | 6/2005 | Nieminen et al. |
| 2005/0137450 A1 | 6/2005 | Aronson et al. |
| 2005/0137451 A1 | 6/2005 | Gordon et al. |
| 2005/0149182 A1 | 7/2005 | Alferness et al. |
| 2005/0197692 A1 | 9/2005 | Pai et al. |
| 2005/0197693 A1 | 9/2005 | Pai et al. |
| 2005/0197694 A1 | 9/2005 | Pai et al. |
| 2005/0209690 A1 | 9/2005 | Mathis et al. |
| 2005/0216077 A1 | 9/2005 | Mathis et al. |
| 2005/0261704 A1 | 11/2005 | Mathis |
| 2005/0272969 A1 | 12/2005 | Alferness et al. |
| 2006/0030882 A1 | 2/2006 | Adams et al. |
| 2006/0041305 A1 | 2/2006 | Lauterjung |
| 2006/0116758 A1 | 6/2006 | Swinford et al. |
| 2006/0142854 A1 | 6/2006 | Alferness et al. |
| 2006/0161169 A1 | 7/2006 | Nieminen et al. |
| 2006/0167544 A1 | 7/2006 | Nieminen et al. |
| 2006/0173536 A1 | 8/2006 | Mathis et al. |
| 2006/0271174 A1 | 11/2006 | Nieminen et al. |
| 2006/0276891 A1 | 12/2006 | Nieminen et al. |
| 2007/0066879 A1 | 3/2007 | Mathis et al. |
| 2007/0239270 A1 | 10/2007 | Mathis et al. |
| 2008/0015407 A1 | 1/2008 | Mathis et al. |
| 2008/0015679 A1 | 1/2008 | Mathis et al. |
| 2008/0015680 A1 | 1/2008 | Mathis et al. |
| 2010/0280602 A1 | 11/2010 | Mathis |
| 2011/0066234 A1 | 3/2011 | Gordon et al. |
| 2011/0106117 A1 | 5/2011 | Mathis et al. |
| 2011/0308367 A1 | 12/2011 | Hayner et al. |
| 2012/0123532 A1 | 5/2012 | Mathis |
| 2012/0197389 A1 | 8/2012 | Alferness et al. |
| 2016/0374806 A1 | 12/2016 | Mathis et al. |
| 2016/0374807 A1 | 12/2016 | Mathis et al. |
| 2016/0374808 A1 | 12/2016 | Mathis et al. |
| 2016/0374809 A1 | 12/2016 | Mathis et al. |
| 2016/0374810 A1 | 12/2016 | Mathis et al. |
| 2017/0079796 A1 | 3/2017 | Nieminen et al. |
| 2017/0189185 A1 | 7/2017 | Nieminen et al. |
| 2017/0296341 A1 | 10/2017 | Nieminen et al. |

FOREIGN PATENT DOCUMENTS

| | | |
|---|---|---|
| SE | 9902455 | 12/2000 |
| WO | WO98/56435 A1 | 12/1998 |
| WO | WO00/44313 A1 | 8/2000 |
| WO | WO00/60995 A2 | 10/2000 |
| WO | WO00/74603 A1 | 12/2000 |
| WO | WO01/00111 A1 | 1/2001 |
| WO | WO01/19292 A1 | 3/2001 |
| WO | WO01/50985 A1 | 7/2001 |
| WO | WO01/54618 A1 | 8/2001 |
| WO | WO01/87180 A2 | 11/2001 |
| WO | WO02/00099 A2 | 1/2002 |
| WO | WO02/01999 A2 | 1/2002 |
| WO | WO02/05888 A1 | 1/2002 |
| WO | WO02/19951 A1 | 3/2002 |
| WO | WO02/34118 A2 | 5/2002 |
| WO | WO02/47539 A2 | 6/2002 |
| WO | WO02/053206 A2 | 7/2002 |
| WO | WO02/060352 A1 | 8/2002 |
| WO | WO02/062263 A2 | 8/2002 |
| WO | WO02/062270 A1 | 8/2002 |

(56) References Cited

FOREIGN PATENT DOCUMENTS

| WO | WO02/062408 A2 | 8/2002 |
| --- | --- | --- |
| WO | WO02/076284 A2 | 10/2002 |
| WO | WO02/078576 A2 | 10/2002 |
| WO | WO02/096275 A2 | 12/2002 |
| WO | WO03/015611 A2 | 2/2003 |
| WO | WO03/037171 A2 | 5/2003 |
| WO | WO03/049647 A1 | 6/2003 |
| WO | WO03/049648 A2 | 6/2003 |
| WO | WO03/055417 A1 | 7/2003 |
| WO | WO03/059198 A2 | 7/2003 |
| WO | WO03/063735 A2 | 8/2003 |

OTHER PUBLICATIONS

Gray, H. Anatomy of the Human Body. The Systemic Veins. Philadelphia: Lea & Febiger, 1918; Bartleby.com. 2000. Available at www.bartleby.com/107/. Accessed Jun. 7, 2006.

Heartsite.com. Echocardiogram, 1999; p. 1-4. A.S.M. Systems Inc. Available at: http://www.heartsite.com/html/echocardiogram.html. Accessed Jul. 1, 2005.

Papageorgiou, P., et al. Coronary Sinus Pacing Prevents Induction of Atrial Fibrillation. Circulation. Sep. 16, 1997; 96(6): 1893-1898.

Pelton et al. Medical uses of nitinol; Material Science Forum; vols. 327-328; pp. 63-70; 2000 (held in Kanazawa, Japan, May 1999).

Pijls et al.; Measurement of fractional flow reserve to assess the functional severity of coronary-artery stenoses; The New England J. of Med.; vol. 334; No. 26; pp. 1703-1708; Jun. 27, 1996.

Pai, Suresh; U.S. Appl. No. 60/329,694 entitled "Percutaneous cardiac support structures and deployment means," filed Oct. 16, 2001.

Yamanouchi, et al.; Activation Mapping from the coronary sinus may be limited by anatomic variations; vol. 21 pp. 2522-2526; Nov. 1998.

Nieminen et al.; U.S. Appl. No. 15/136,739 entitled "Tissue shaping device," filed Apr. 22, 2016.

Mathis et al.; U.S. Appl. No. 15/230,060 entitled "Fixed anchor and pull mitral device and method," filed Aug. 5, 2016.

Wypych; U.S. Appl. No. 15/453,734 entitled "Methods and devices for reducing paravalvular leakage," filed Mar. 8, 2017.

FIXED ANCHOR AND PULL MITRAL VALVE DEVICE AND METHOD

CROSS-REFERENCE TO RELATED APPLICATIONS

This application is a continuation of U.S. patent application Ser. No. 12/016,054, filed Jan. 17, 2008, now U.S. Pat. No. 9,408,695, which is a divisional of application Ser. No. 11/132,788, filed May 18, 2005, abandoned; which is a continuation of application Ser. No. 10/066,426, filed Jan. 30, 2002, now U.S. Pat. No. 6,976,995. These applications are incorporated by reference in their entirety as if fully set forth herein.

FIELD OF THE INVENTION

The present invention generally relates to a device and method for treating dilated cardiomyopathy of a heart. The present invention more particularly relates to a device and method for reshaping the mitral valve annulus.

BACKGROUND OF THE INVENTION

The human heart generally includes four valves. Of these valves, a most critical one is known as the mitral valve. The mitral valve is located in the left atrial ventricular opening between the left atrium and left ventricle. The mitral valve is intended to prevent regurgitation of blood from the left ventricle into the left atrium when the left ventricle contracts. In preventing blood regurgitation the mitral valve must be able to withstand considerable back pressure as the left ventricle contracts.

The valve cusps of the mitral valve are anchored to muscular wall of the heart by delicate but strong fibrous cords in order to support the cusps during left ventricular contraction. In a healthy mitral valve, the geometry of the mitral valve ensures that the cusps overlie each other to preclude regurgitation of the blood during left ventricular contraction.

The normal functioning of the mitral valve in preventing regurgitation can be impaired by dilated cardiomyopathy caused by disease or certain natural defects. For example, certain diseases may cause dilation of the mitral valve annulus. This can result in deformation of the mitral valve geometry to cause ineffective closure of the mitral valve during left ventricular contraction. Such ineffective closure results in leakage through the mitral valve and regurgitation. Diseases such as bacterial inflammations of the heart or heart failure can cause the aforementioned distortion or dilation of the mitral valve annulus. Needless to say, mitral valve regurgitation must not go uncorrected.

One method of repairing a mitral valve having impaired function is to completely replace the valve. This method has been found to be particularly suitable for replacing a mitral valve when one of the cusps has been severely damaged or deformed. While the replacement of the entire valve eliminates the immediate problem associated with a dilated mitral valve annulus, presently available prosthetic heart valves do not possess the same durability as natural heart valves.

Various other surgical procedures have been developed to correct the deformation of the mitral valve annulus and thus retain the intact natural heart valve function. These surgical techniques involve repairing the shape of the dilated or deformed valve annulus. Such techniques, generally known as annuloplasty, require surgically restricting the valve annulus to minimize dilation. Here, a prosthesis is typically sutured about the base of the valve leaflets to reshape the valve annulus and restrict the movement of the valve annulus during the opening and closing of the mitral valve.

Many different types of prostheses have been developed for use in such surgery. In general, prostheses are annular or partially annular shaped members which fit about the base of the valve annulus. The annular or partially annular shaped members may be formed from a rigid material, such as a metal, or from a flexible material.

While the prior art methods mentioned above have been able to achieve some success in treating mitral regurgitation, they have not been without problems and potential adverse consequences. For example, these procedures require open heart surgery. Such procedures are expensive, are extremely invasive requiring considerable recovery time, and pose the concomitant mortality risks associated with such procedures. Moreover, such open heart procedures are particularly stressful on patients with a comprised cardiac condition. Given these factors, such procedures are often reserved as a last resort and hence are employed late in the mitral regurgitation progression. Further, the effectiveness of such procedures is difficult to assess during the procedure and may not be known until a much later time. Hence, the ability to make adjustments to or changes in the prostheses to obtain optimum effectiveness is extremely limited. Later corrections, if made at all, require still another open heart surgery.

An improved therapy to treat mitral regurgitation without resorting to open heart surgery has recently been proposed. This is rendered possible by the realization that the coronary sinus of a heart is near to and at least partially encircles the mitral valve annulus and then extends into a venous system including the great cardiac vein. As used herein, the term "coronary sinus" is meant to refer to not only the coronary sinus itself but in addition, the venous system associated with the coronary sinus including the great cardiac vein. The therapy contemplates the use of a device introduced into the coronary sinus to reshape and advantageously affect the geometry of the mitral valve annulus.

The device includes a resilient member having a cross sectional dimension for being received within the coronary sinus of the heart and a longitudinal dimension having an unstressed arched configuration when placed in the coronary sinus. The device partially encircles and exerts an inward pressure on the mitral valve. The inward pressure constricts the mitral valve annulus, or at least a portion of it, to essentially restore the mitral valve geometry. This promotes effective valve sealing action and eliminates mitral regurgitation.

The device may be implanted in the coronary sinus using only percutaneous techniques similar to the techniques used to implant cardiac leads such as pacemaker leads. One proposed system for implanting the device includes an elongated introducer configured for being releasably coupled to the device. The introducer is preferably flexible to permit it to advance the device into the heart and into the coronary sinus through the coronary sinus ostium. To promote guidance, an elongated sheath is first advanced into the coronary sinus. Then, the device and introducer are moved through a lumen of the sheath until the device is in position within the coronary sinus. Because the device is formed of resilient material, it conforms to the curvatures of the lumen as it is advanced through the sheath. The sheath is then partially retracted to permit the device to assume its unstressed arched configuration. Once the device is properly positioned, the introducer is then decoupled from the device and retracted through the sheath. The procedure is then completed by the retraction of the sheath. As a result, the device is left within the coronary sinus to exert the inward pressure on the mitral valve to restore mitral valve geometry.

The foregoing therapy has many advantages over the traditional open heart surgery approach. Since the device, system and method may be employed in a comparatively noninvasive procedure, mitral valve regurgitation may be treated at an early stage in the mitral regurgitation progression. Further, the device may be placed with relative ease by any minimally invasive cardiologist. Still further, since the heart remains completely intact throughout the procedure, the effectiveness of the procedure may be readily determined. Moreover, should adjustments be deemed desirable, such adjustments may be made during the procedure and before the patient is sent to recovery.

Another approach to treat mitral regurgitation with a device in the coronary sinus is based upon the observation that the application of a localized force against a discrete portion of the mitral valve annulus can terminate mitral regurgitation. This suggests that mitral valve dilation may be localized and nonuniform. Hence, the device applies a force to one or more discrete portions of the atrial wall of the coronary sinus to provide localized mitral valve annulus reshaping instead of generalized reshaping of the mitral valve annulus. Such localized therapy would have all the benefits of the generalized therapy. In addition, a localized therapy device may be easier to implant and adjust.

A still further approach to treat mitral regurgitation from the coronary sinus of the heart contemplates a device having a first anchor configured to be positioned within and fixed to the coronary sinus of the heart adjacent the mitral valve annulus within the heart, a cable fixed to the first anchor and extending proximally from the first anchor within the heart, a second anchor configured to be positioned in and fixed in the heart proximal to the first anchor and arranged to slidingly receive the cable, and a lock that locks the cable on the second anchor. When the first and second anchors are fixed within the heart, the cable may be drawn proximally and locked on the second anchor. The geometry of the mitral valve is thereby affected. This approach provides flexibility in that the second anchor may be positioned and fixed in the coronary sinus or alternatively, the second anchor may be positioned and fixed in the right atrium. This approach further allows adjustments in the cable tension after implant. The present invention provides a still further alternative for treating mitral regurgitation with a device placed in the coronary sinus adjacent to the mitral valve annulus.

SUMMARY OF THE INVENTION

The present invention provides a device that affects mitral valve annulus geometry of a heart. The device includes a first anchor configured to be positioned within and anchored to the coronary sinus of the heart adjacent the mitral valve annulus within the heart, and a second anchor configured to be positioned within the heart proximal to the first anchor and adjacent the mitral valve annulus within the heart. The device further includes a connecting member having a fixed length permanently attached to the first and second anchors. As a result, when the first and second anchors are within the heart with the first anchor anchored in the coronary sinus, the second anchor may be displaced proximally to affect the geometry of the mitral valve annulus and released to maintain the effect on the mitral valve geometry. The second anchor may be configured, when deployed, to anchor against distal movement but be movable proximally to permit the second anchor to be displaced proximally within the coronary sinus.

The first anchor and the second anchor are preferably self-deploying upon release in the coronary sinus or may be deployable after placement. Further, the connecting member, in being of fixed length, has a maximum extended length and as such may be a rigid member, have an initial arcuate configuration, include a spring, having a maximum length or be flexible but not stretchable.

The present invention further provides a device for affecting mitral valve annulus geometry of a heart. The device includes first anchor means for anchoring in the coronary sinus of the heart adjacent the mitral valve annulus, and second anchor means for being deployed within the heart proximal to the first anchor means and adjacent the mitral valve annulus, and connecting means having a fixed length and permanently connecting the first anchor means to the second anchor means. As a result, when the first and second anchor means are within the heart with the first anchor means anchored in the coronary sinus, the second anchor means may be displaced proximally for cooperating with the first anchor means and the connecting means for affecting the geometry of the mitral valve annulus and released for maintaining the effect on the mitral valve geometry.

The invention further provides a system that affects mitral valve annulus geometry of a heart. The system includes a mitral valve device including a first anchor configured to be positioned within and anchored to the coronary sinus of the heart adjacent the mitral valve annulus within the heart, a second anchor configured to be positioned within the heart proximal to the first anchor and adjacent the mitral valve annulus within the heart, and a connecting member having a fixed length permanently attached to the first and second anchors.

The system further includes a catheter having a distal end, a proximal end and a lumen that receives the device, the catheter being guidable into the coronary sinus adjacent to the mitral valve annulus and deploying the first and second anchors of the device within the coronary sinus adjacent to the mitral valve annulus, and a tether releasably coupled to the second anchor and extending proximally through the lumen and out of the catheter proximal end. As a result, when the first anchor is deployed by the catheter in the coronary sinus, the second anchor may be displaced proximally by proximally pulling on the tether to affect the geometry of the mitral valve annulus and thereafter released for deployment to maintain the effect on the mitral valve geometry.

The present invention further provides a method of affecting mitral valve annulus geometry in a heart. The method includes the steps of fixing a first anchor within the coronary sinus of the heart adjacent to the mitral valve annulus, positioning a second anchor within the coronary sinus adjacent to the mitral valve annulus and proximal to the first anchor, fixing a fixed length connecting member between the first anchor and the second anchor, displacing the second anchor proximally to affect the geometry of the mitral valve annulus, and releasing the second anchor from further proximal displacement to maintain the effect on the mitral valve geometry.

The present invention further provides a device that affects mitral valve annulus geometry of a heart. The device includes a first anchor configured to be positioned within and anchored to the coronary sinus of the heart adjacent the mitral valve annulus within the heart, a second anchor configured to be positioned within the heart proximal to the first anchor and adjacent the mitral valve annulus within the heart, and a connecting member attached between the first and second anchors. At least one of the first and second anchors anchoring against movement in a first direction and being movable in a second direction opposite the first direction.

The at least one anchor may be the first anchor wherein the first direction is a proximal direction and wherein the second direction is a distal direction. The at least one anchor may be the second anchor wherein the first direction is a distal direction and wherein the second direction is a proximal direction. In a preferred embodiment, the first anchor anchors against movement in a proximal direction and is movable in a distal direction and the second anchor anchors against movement in the distal direction and is movable in the proximal direction.

The invention still further provides a device that affects mitral valve annulus geometry of a heart and which permits a cardiac lead to be implanted in the left side of the heart. The device includes a first anchor configured to be positioned within and anchored to the coronary sinus of the heart adjacent the mitral valve annulus within the heart, a second anchor configured to be positioned within the heart proximal to the first anchor and adjacent the mitral valve annulus within the heart, and a connecting member attached between the first and second anchors. The first anchor is configured to occupy less than all of the coronary sinus to permit a cardiac lead to be passed by the first anchor.

The first anchor may include a loop through which the cardiac lead may be passed. The second anchor may be positionable within the coronary sinus and be configured to occupy less than all of the coronary sinus to permit the cardiac lead to be passed by the second anchor. The second anchor may also include a loop through which the cardiac lead may be passed.

BRIEF DESCRIPTION OF THE DRAWINGS

The features of the present invention which are believed to be novel are set forth with particularity in the appended claims. The invention, together with further aspects and advantages thereof, may best be understood by making reference to the following description taken in conjunction with the accompanying drawings, in the several figures of which like reference numerals identify identical elements, and wherein:

DETAILED DESCRIPTION OF THE INVENTION

Figure 1:
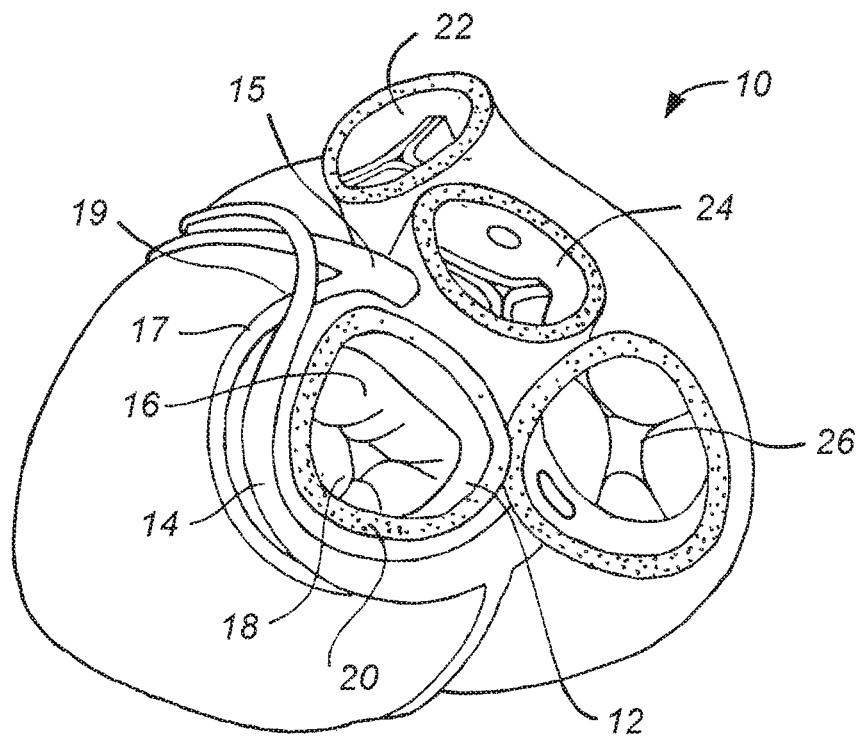
FIG. 1 is a superior view of a human heart with the atria removed.

Referring now to FIG. 1, it is a superior view of a human heart 10 with the atria removed to expose the mitral valve 12, the coronary sinus 14, the coronary artery 15, and the circumflex artery 17 of the heart 10 to lend a better understanding of the present invention. Also generally shown in FIG. 1 are the pulmonary valve 22, the aortic valve 24, and the tricuspid valve 26 of the heart 10.

The mitral valve 12 includes an anterior cusp 16, a posterior cusp 18 and an annulus 20. The annulus encircles the cusps 16 and 18 and maintains their spacing to provide a complete closure during a left ventricular contraction. As is well known, the coronary sinus 14 partially encircles the mitral valve 12 adjacent to the mitral valve annulus 20. As is also known, the coronary sinus is part of the venous system of the heart and extends along the AV groove between the left atrium and the left ventricle. This places the coronary sinus essentially within the same plane as the mitral valve annulus making the coronary sinus available for placement of the mitral valve therapy device of the present invention therein.

Figure 2:
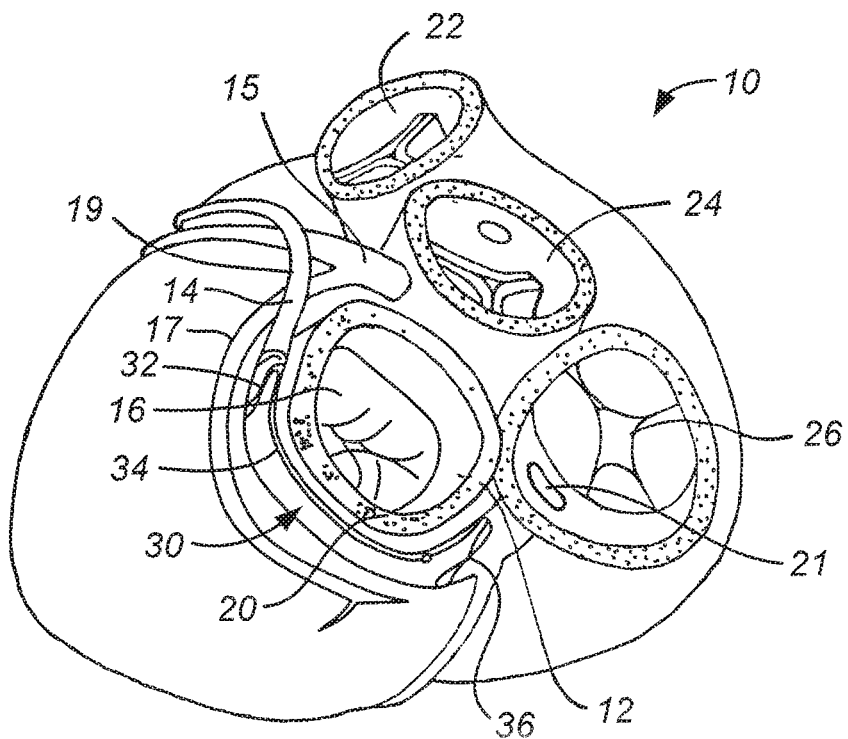
FIG. 2 is a superior view of a human heart similar to FIG. 1 illustrating a deployed mitral valve device embodying the present invention.

FIG. 2 shows a mitral valve therapy device 30 embodying the present invention. As may be noted in FIG. 2, the device 30 includes a first anchor 32, a connecting member 34, and a second anchor 36. The anchors 32 and 36 and the connecting member 34 may be formed from the same material to provide an integral structure.

The first anchor 32 is located at the distal end of the device 30. The anchor 32 is hook-shaped so as to be self-deployable when released in the coronary sinus 14. More specifically, the device 30 may be formed of most any biocompatible material such as stainless steel, Nitinol, a nickel/titanium alloy of the type well known in the art having shape memory or plastic. The hook-shaped configuration of the anchor 32 thus expands when released to wedge against the inner wall of the coronary sinus 14 for anchoring or fixing the anchor 32 against at least proximal movement. The anchor 32 may however allow distal movement. Preferably, the anchor 32 is positioned just proximally to the crossover point 19 of the coronary sinus 14 and a circumflex artery 17.

The connecting member 34, by being formed of Nitinol, is relatively rigid and is predisposed to have an arcuate configuration to generally correspond to the shape of the mitral valve annulus 20. The connecting member 34 is of a fixed length and is permanently attached to the first and second anchors 32 and 36. Here it will be noted that the second anchor is positioned within the coronary sinus just distal to the ostium 21 of the coronary sinus 14. The second anchor 36 may have a similar hook-shaped configuration and is also preferably self-expanding to be self-deployable. The hook-shape of the anchor 36 anchors or fixes the anchor 36 against distal movement but permits the anchor to be pulled proximally. This is a particularly significant aspect of the device 30 because it permits the device to be adjusted after the anchors 32 and 36 are first deployed.

When the device 30 is deployed as shown in FIG. 2, the first anchor 32 is fixed against proximal movement within the coronary sinus 14. The connecting member 34 then extends proximally from the first anchor 32 to the second anchor 36. The second anchor 36 is then positioned in its desired location within the coronary sinus 14 proximal to the first anchor 32 and permitted to self-expand for being anchored against distal movement. Then, the second anchor 36 is pulled proximally while the first anchor 32 is held in its fixed position. This creates tension in the connecting member 34 to affect the geometry of the mitral valve annulus 20. Once a desired amount of tension is applied to the connecting member 34, the second anchor 36 is released from further movement and is redeployed against distal movement. With the connecting member 34 now under maintained tension, the advantageously affected geometry of the mitral valve annulus 20 is now preserved. The tension in the cable is preferably adjusted by the pulling on the second anchor 26 while monitoring a parameter indicative of mitral regurgitation, such as Doppler echo.

The connecting member 34 may be provided with a covering (not shown). The covering may preferably be formed of a compressible material to serve to cushion the forces of the connecting member applied against the inner wall of the coronary sinus 14.

Figure 3:
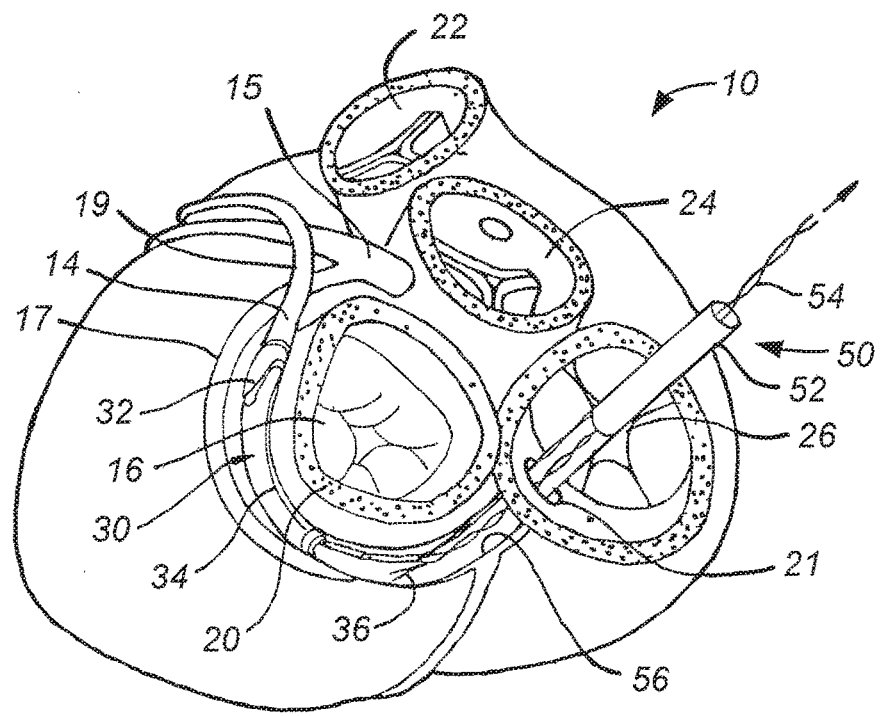
FIG. 3 is a superior view of a human heart similar to FIG. 2 illustrating a first step in the deployment of the mitral valve device of FIG. 2 embodying the present invention.
Figure 4:
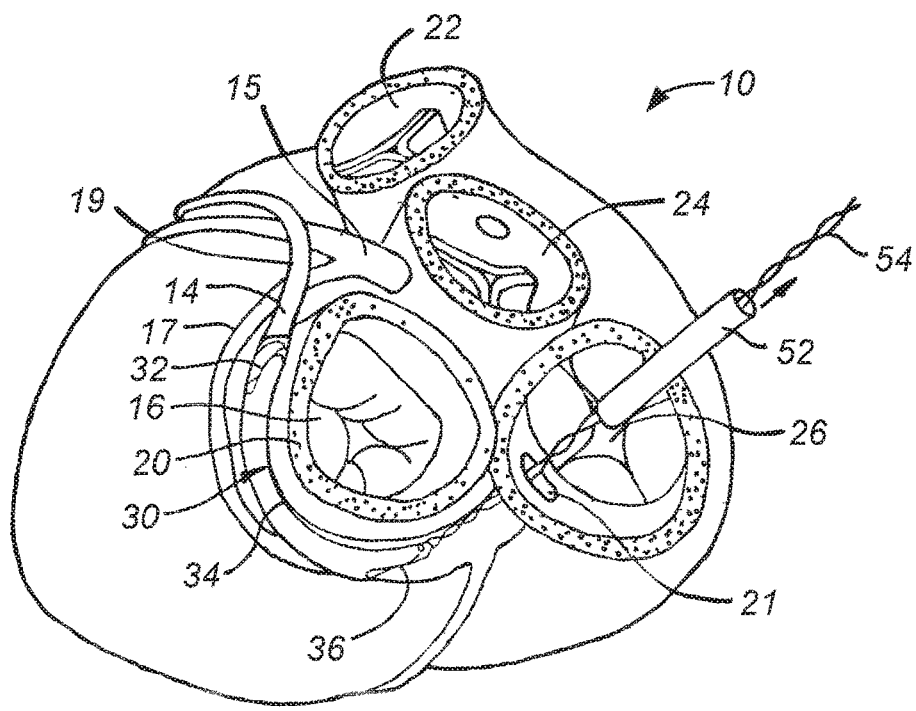
FIG. 4 is a view similar to FIG. 3 illustrating a further step in the deployment of the device of FIG. 2.
Figure 5:
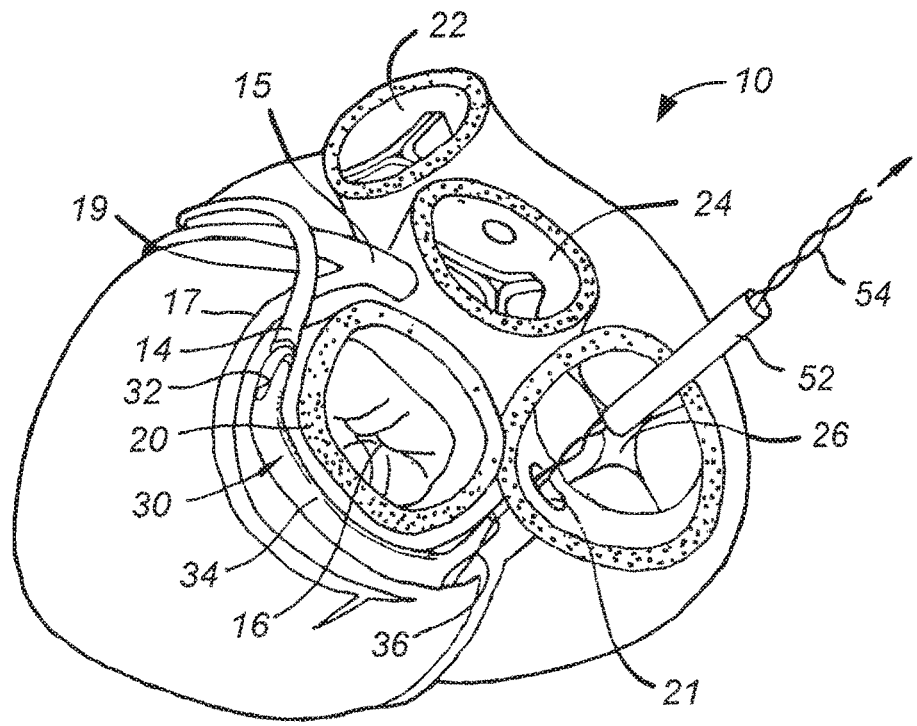
FIG. 5 is a view similar to FIG. 3 illustrating a final step in the deployment of the device of FIG. 2.

FIGS. 3 through 5 show a manner in which the device 30 may be deployed by a deployment assembly 50. As will be noted in FIG. 3, the deployment assembly 50 includes a catheter 52 and a tether 54. The catheter 52 has a lumen 56 dimensioned for slidably receiving the device 30 in its predeployed state with the tether 54 looped around the second anchor 36 and extending out the proximal end of the catheter 52.

As will be noted in FIG. 3, the first anchor 32 has been deployed while the second anchor remains in the catheter lumen 56. This may be accompanied by feeding the catheter 52 into the coronary sinus until the first anchor is in a desired position. Now, the catheter 52 may be moved proximally while maintaining the first anchor 32 against movement. Proximal movement of the catheter 52 will release the anchor 32. When the anchor is released, it will self-expand to self-deploy and be fixed against proximal movement.

As shown in FIG. 4, the catheter 52 is further retracted to release the second anchor 36 to permit it to self-expand and to self-deploy. The second anchor 36 is now fixed against distal movement but permitted to move proximally. The tether 54 continues to extend out the proximal end of the catheter 52.

As may now be further seen in FIG. 5, tension is then applied to the connecting member 34 by proximally pulling on the tether 54, and hence the second anchor 36, while the first anchor 32 resists proximal movement. When the desired tension is placed on the connecting member 34, the second anchor 36 is released for re-self-deployment. When this is completed, the first anchor 32 and the second anchor 36 are fixed in position with a tension in the connecting member 34. The catheter 52 and the tether 54 may then be removed to complete the deployment process. Although the proximal anchor 36 is shown to be finally deployed in the coronary sinus, it will be appreciated by those skilled in the art that the proximal anchor 36, after being displaced proximally, may finally be deployed within the right atrium just proximal to the ostium 21 of the coronary sinus 14. Hence, any final position of the proximal anchor 36 proximal to the distal anchor 32 and within the heart is contemplated in accordance with the present invention.

In accordance with the present invention, the device 30 may be deployed in a slightly different manner as described above. Here, the first anchor 32 may be deployed as described above and the second anchor 36 left in the catheter 52 as it is moved proximally. When the second anchor 36 reaches a desired position, the catheter 52 may then be pulled back to release and deploy the second anchor 36. As a result, in accordance with this alternative embodiment, the second anchor, when deployed, may anchor against both distal and proximal movement.

Figure 6:
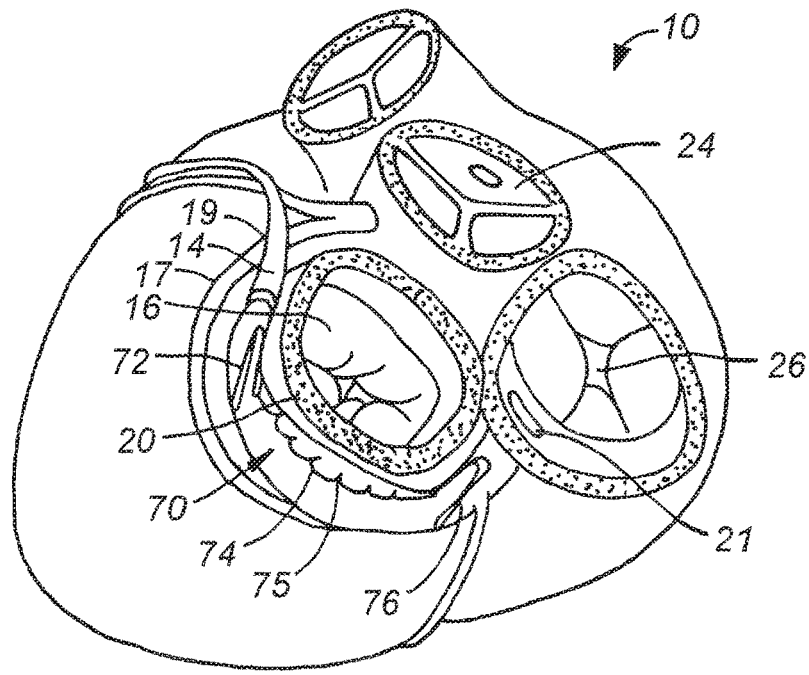
FIG. 6 is a superior view of a human heart similar to FIG. 1 illustrating another deployed mitral valve device embodying the present invention.

FIG. 6 shows another mitral valve device 70 embodying the present invention. The device 70 is similar to the device 30 previously described except that its connecting member 74 includes a spring configuration 75. The spring 75 has a maximum length and serves to more forcefully maintain the applied tension on the mitral valve annulus 20. To this end, the device 70 includes a first anchor 72, the connecting member 74, and a second anchor 76.

The first and second anchors 72 and 76 are again configured so that when they are released, they self-expand, to wedge against the inner wall of the coronary sinus 14. Again, the first anchor resists proximal movement and the second anchor 76 resists distal movement. In all other respects, the device 70 may be identical to and deployed in the same manner as the device 30.

Implantable cardiac stimulation devices are well known in the art. Such devices may include, for example, implantable cardiac pacemakers and defibrillators. The devices are generally implanted in a pectoral region of the chest beneath the skin of a patient within what is known as a subcutaneous pocket. The implantable devices generally function in association with one or more electrode carrying leads which are implanted within the heart. The electrodes are usually positioned within the right side of the heart, either within the right ventricle or right atrium, or both, for making electrical contact with their respective heart chamber. Conductors within the leads and a proximal connector carried by the leads couple the electrodes to the device to enable the device to sense cardiac electrical activity and deliver the desired therapy.

Traditionally, therapy delivery had been limited to the venous, or right side of the heart. The reason for this is that implanted electrodes can cause blood clot formation in some patients. If a blood clot were released arterially from the left heart, as for example the left ventricle, it could pass directly to the brain potentially resulting in a paralyzing or fatal stroke. However, a blood clot released from the right heart, as from the right ventricle, would pass into the lungs where the filtering action of the lungs would prevent a fatal or debilitating embolism in the brain.

Recently, new lead structures and methods have been proposed and even practiced for delivering cardiac rhythm management therapy to the left heart. These lead structures and methods avoid direct electrode placement within the left atrium and left ventricle of the heart by lead implantation within the coronary sinus of the heart. As previously mentioned, the phrase "coronary sinus" refers to not only the coronary sinus itself but in addition, the venous system associated with the coronary sinus including the great cardiac vein.

It has been demonstrated that electrodes placed in the coronary sinus region of the heart may be used for left atrial pacing, left ventricular pacing, or cardioversion and defibrillation. These advancements enable implantable cardiac stimulation devices to address the needs of a patient population with left ventricular dysfunction and/or congestive heart failure which would benefit from left heart side pacing, either alone or in conjunction with right heart side pacing (bi-chamber pacing), and/or defibrillation.

Figure 7:
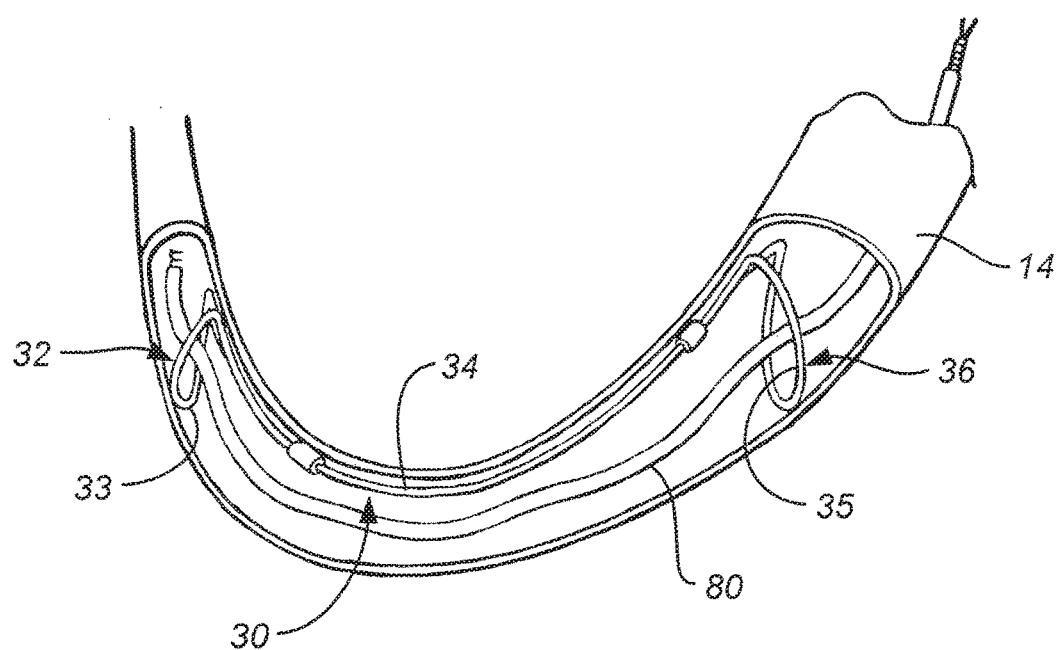
FIG. 7 is a side view with a portion broken away illustrating further details of device anchors and the manner in which they permit an implantable lead to pass thereby.

Even though the device of the present invention is implantable in the coronary sinus of the heart, it is configured in accordance with further aspects of the present invention to permit a cardiac lead to pass through the coronary sinus for functioning as described above. To that end, and as best seen in FIG. 7, the anchors 32 and 36 of the device 30 occupy only a small portion of and hence less than all of the interior space of the coronary sinus 14. This permits a cardiac lead 80 to be advanced into the coronary sinus 14 for implant in the left side of the heart.

More specifically, the anchors 32 and 36 take the form of loops 33 and 35 respectively which are then bent backwards on the device to form the previously referred to hook-shapes for self-deployment. The loops 33 and 35 thus permit the cardiac lead 80 to be passed therethrough for implant in the left heart. This is particularly desirable because many patients suffering from mitral regurgitation may also be candidates for left heart cardiac rhythm management therapy.

While particular embodiments of the present invention have been shown and described, modifications may be made, and it is therefore intended in the appended claims to cover all such changes and modifications which fall within the true spirit and scope of the invention as defined by the appended claims.

What is claimed is:

1. A device for treating mitral valve regurgitation, comprising:
   a distal expandable anchor, a proximal expandable anchor, a fixed length connecting member extending from the proximal expandable anchor to the distal expandable anchor, a distal end, a proximal end, and an axis that extends between the distal and proximal ends and along the connecting member,
   wherein at least one of the proximal and distal anchors comprises first and second arm segments and has an expanded configuration, wherein in the expanded configuration the first and second arm segments extend from one of the distal and proximal ends of the device away from one another, radially outward, and axially toward the connector, and then meet one another at an anchor apex that is axially spaced from the one of the distal and proximal ends of the device, the anchor apex being disposed in an anchor portion that is spaced radially furthest away from the axis.

2. The device of claim 1 wherein the distal expandable anchor comprises the first and second arms segments and the one of the distal and proximal ends is the distal end, such that in the expanded configuration the first and second arm segments extend away from one another at the distal end of the device, proximally toward the connector, and then meet one another at the anchor apex that is proximal to the distal end.

3. The device of claim 1 wherein the proximal expandable anchor comprises the first and second arms segments and the one of the distal and proximal ends is the proximal end, such that in the expanded configuration the first and second arm segments extend away from one another at the proximal end of the device, distally toward the connector, and then meet one another at the anchor apex that is distal to the proximal end.

4. A device for treating mitral valve regurgitation, comprising:
   a distal expandable anchor, a proximal expandable anchor, a fixed length connecting member extending from the proximal expandable anchor to the distal expandable anchor, a distal end, a proximal end, and an axis that extends between the distal and proximal ends and along the connecting member,
   wherein at least one of the proximal and distal anchors comprises first and second arm segments and has an expanded configuration, wherein in the expanded configuration the first and second arm segments diverge relative to one another, then extend radially outward and axially, and then meet one another at an anchor apex that is axially spaced from where the first and second segments diverge relative to one another, the anchor apex being disposed in an anchor portion that is spaced radially furthest away from the axis.

5. The device of claim 4, wherein the distal expandable anchor comprises the first and second arm segments, and in the expanded configuration the first and second arm segments, after diverging relative to one another, extend radially outward and proximally toward the connecting member, and then meet one another at the anchor apex that is proximal to a distal end of the device.

6. The device of claim 4, wherein the proximal expandable anchor comprises the first and second arm segments, and in the expanded configuration the first and second arm segments, after diverging relative to one another, extend radially outward and distally toward the connecting member, and then meet one another at the anchor apex that is distal to a proximal end of the device.

* * * * *